US008065015B2

(12) United States Patent
Brighton et al.

(10) Patent No.: US 8,065,015 B2
(45) Date of Patent: *Nov. 22, 2011

(54) REGULATION OF GENES VIA APPLICATION OF SPECIFIC AND SELECTIVE ELECTRICAL AND ELECTROMAGNETIC SIGNALS

(75) Inventors: Carl T. Brighton, Malvern, PA (US); Solomon R. Pollack, North Wales, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 568 days.

This patent is subject to a terminal disclaimer.

(21) Appl. No.: 12/167,283

(22) Filed: Jul. 3, 2008

(65) Prior Publication Data

US 2008/0269838 A1     Oct. 30, 2008

Related U.S. Application Data

(63) Continuation of application No. 10/257,126, filed as application No. PCT/US01/05991 on Feb. 23, 2001, now Pat. No. 7,465,566.

(60) Provisional application No. 60/184,491, filed on Feb. 23, 2000.

(51) Int. Cl.
*C12N 13/00* (2006.01)

(52) U.S. Cl. .................................... 607/50; 435/173.8

(58) Field of Classification Search ........................ None
See application file for complete search history.

(56) References Cited

U.S. PATENT DOCUMENTS

| | | | |
|---|---|---|---|
| 4,430,999 A | 2/1984 | Brighton et al. | 128/419 |
| 4,442,846 A | 4/1984 | Brighton et al. | 128/784 |
| 4,467,808 A | 8/1984 | Brighton et al. | 128/419 |
| 4,467,809 A | 8/1984 | Brighton et al. | 607/51 |
| 4,487,834 A | 12/1984 | Brighton | 435/173 |
| 4,506,674 A | 3/1985 | Brighton et al. | 128/419 |
| 4,509,520 A | 4/1985 | Dugot | 128/419 |
| 4,535,775 A | 8/1985 | Brighton et al. | 128/419 F |
| 4,549,547 A | 10/1985 | Brighton et al. | 128/419 |
| 4,600,010 A | 7/1986 | Dugot | 128/419 |
| 4,683,873 A | 8/1987 | Cadossi et al. | 128/1.5 |
| 4,998,532 A | 3/1991 | Griffith | 128/419 |
| 5,014,699 A | 5/1991 | Pollack et al. | 128/419 |
| 5,038,797 A | 8/1991 | Batters | 128/798 |
| 5,269,746 A | 12/1993 | Jacobson | |
| 5,273,033 A | 12/1993 | Hoffman | 607/46 |
| 5,338,286 A | 8/1994 | Abbott et al. | 600/14 |
| 5,374,283 A | 12/1994 | Flick | 607/46 |
| 5,743,844 A | 4/1998 | Tepper et al. | 600/14 |
| 5,968,527 A | 10/1999 | Litovitz | 424/400 |
| 6,083,149 A | 7/2000 | Wascher et al. | 600/9 |
| 6,132,362 A | 10/2000 | Tepper et al. | 600/14 |
| 6,186,940 B1 | 2/2001 | Kirschbaum | 600/12 |
| 6,261,221 B1 | 7/2001 | Tepper et al. | 600/14 |
| 6,292,699 B1 | 9/2001 | Simon et al. | 607/51 |
| 6,485,963 B1 | 11/2002 | Wolf et al. | 435/298.2 |
| 6,605,089 B1 | 8/2003 | Michelson | 606/61 |
| 6,747,004 B1 | 6/2004 | Tabibzadeh | 514/12 |
| 6,919,205 B2 * | 7/2005 | Brighton | 435/375 |
| 6,955,642 B1 | 10/2005 | Simon | 600/14 |
| 7,022,506 B2 | 4/2006 | Brighton et al. | 435/173.8 |
| 7,130,692 B2 * | 10/2006 | Brighton et al. | 607/50 |
| 7,158,835 B2 | 1/2007 | Brighton et al. | 607/51 |
| 7,167,753 B2 | 1/2007 | Brighton et al. | 607/51 |
| 7,215,995 B2 * | 5/2007 | Brighton et al. | 607/2 |
| 7,374,916 B2 * | 5/2008 | Brighton | 435/173.8 |
| 7,429,471 B2 * | 9/2008 | Brighton | 435/173.8 |
| 7,465,546 B2 * | 12/2008 | Brighton | 435/6 |
| 7,465,566 B2 * | 12/2008 | Brighton et al. | 435/173.8 |
| 2002/0009797 A1 | 1/2002 | Wolf et al. | |
| 2002/0038137 A1 | 3/2002 | Stein | 607/46 |
| 2002/0052634 A1 | 5/2002 | March | 607/50 |
| 2002/0125769 A1 | 9/2002 | Riley et al. | 303/138 |
| 2003/0211084 A1 | 11/2003 | Brighton et al. | 424/93.7 |
| 2004/0138709 A1 | 7/2004 | Brighton | 607/2 |
| 2005/0049640 A1 | 3/2005 | Gurtner et al. | |
| 2005/0203591 A1 | 9/2005 | Brighton | 607/61 |
| 2006/0190043 A1 | 8/2006 | Brighton et al. | 607/2 |
| 2006/0235473 A1 | 10/2006 | Brighton | 607/2 |
| 2007/0299472 A1 | 12/2007 | Brighton | 607/2 |

FOREIGN PATENT DOCUMENTS

EP          0652028         5/1995

(Continued)

OTHER PUBLICATIONS

Carter et al., "Theoretical determination of the current density distributions in human vertebral bodies during electrical stimulation", IEEE Trans Biomed Eng., Jun. 1990, 37(6), 606-614.

Aaron, R.K., et al., "The conservative treatment of osteonecrosis of the femoral head," *Clin. Orthop.*, 1989, 249, 209-218.

Aaron, R.K., et al., "Stimulation of experimental endochondral ossification by low-energy pulsing electromagnetic fields," *J. Bone Miner. Res.*, Nov. 2, 1989, 4, 227-233.

Ala-aho, et al., "Targeted inhibition of human collagenase-3 (MMP-13) expression inhibits squamous cell carcinoma growth in vivo," *Oncogene*, 2004, 23, 5111-5123.

(Continued)

*Primary Examiner* — Jim Ketter
(74) *Attorney, Agent, or Firm* — Woodcock Washburn, LLP

(57) ABSTRACT

Methods and devices for the regulation of gene expression by cells via the application of fields generated by specific and selective electric and electromagnetic signals so as to target diseased or injured tissue for treatment. By gene expression is meant the up regulation or down regulation of the process whereby specific portions (genes) of the human genome (DNA) are transcribed into mRNA and subsequently translated into protein. Methods and devices are provided for the targeted treatment of injured or diseased tissue that include providing specific and selective electric and electromagnetic signals and exposing tissue to the fields generated by the signals so as to regulate gene expression. In particular, methods and devices are provided for the targeted treatment of bone defects, osteoarthritis, osteoporosis, cancer, and other disease states.

8 Claims, 12 Drawing Sheets

FOREIGN PATENT DOCUMENTS

| | | |
|---|---|---|
| EP | 1198580 | 5/2006 |
| JP | H2-195969 | 8/1990 |
| RU | 2147895 C1 | 4/2000 |
| WO | WO 00/02585 A1 | 1/2000 |
| WO | WO 01/62336 A1 | 8/2001 |
| WO | WO 2004/029210 | 8/2004 |
| WO | WO 2005/002667 | 1/2005 |
| WO | WO 2005/070136 A2 | 8/2005 |
| WO | WO 2007/142901 | 12/2007 |

OTHER PUBLICATIONS

Bassett, C.A.L., "Low energy pulsing electromagnetic fields modify biomedical processes," *BioEssays*, 1987, 6(1), 36-42.

Bassett, C.A.L., et al., "Effects of pulsed electromagnetic fields on Steinberg ratings of femoral head osteonecrosis," *Clin. Orthop.*, Sep. 1989, 246, 172-185.

Bassett, C.A.L., et al., "Fundamental and practical aspects of therapeutic uses of pulsed electromagnetic fields (PEMSs)," *Crit. Rev. Biomed. Eng.*, 1989, 17(5), 451-529.

Bassett, C.A.L., et al., "Pulsing electromagnetic field treatment in ununited fractures and failed arthrodeses," *JAMA*, Feb. 5, 1982, 247(5), 623-628.

Binder, A., et al., "Pulsed electromagnetic field therapy of persistent rotator cuff tendonitis," *Lancet*, Mar. 31, 1984, 695-698.

Brighton, C.T., et al., "A multicenter study of the treatment of non-union with constant direct current," *J. Bone and Joint Surgery*, Jan. 1981, 62-A(1), 2-13.

Brighton, C.T., et al., "Treatment of recalcitrant non-union with a capacitively coupled electrical field," *J. Bone and Joint Surgery*, Apr. 1985, 67-A(4), 577-585.

Brighton, C.T., et al., "Treatment of castration-induced osteoporosis by a capacitively coupled electrical signal in rat vertebrae," *J. Bone and Joint Surgery*, Feb. 1989, 71-A(2), 228-236.

Brighton, C.T., et al., "Fracture healing in the rabbit fibula when subjected to various capacitively coupled electrical fields," *J. Orthop. Res.*, 1985, 3, 331-340.

Brighton, C.T., et al., "In vitro bone-cell response to a capacitively coupled electrical field," *Clin. Orthop. Related Res.*, Dec. 1992, 285, 255-262.

Brighton, C.T., et al., "Signal transduction in electrically stimulated bone cells," *J. Bone Joint Surg. Am.*, 2001, 83-A(10), 1514-1523.

Brighton, C.T., et al., "Increased cAMP production after short-term capacitively coupled stimulation in bovine growth plate chondrocytes," *J. Orthop. Res.*, 1988, 6, 552-558.

Brighton, C.T., et al., "Treatment of denervation/disuse osteoporosis in the rat with a capacitively coupled electrical signal: effects on bone formation and bone resorption," *J. Orthop. Res.*, 1988, 6, 676-684.

Brighton, C.T., et al., "Prevention and Treatment of sciatic denervation disuse osteoporosis in rat tibia with capacitively coupled electrical stimulation," *Bone*, 1985, 6, 87-97.

Brighton, C.T., et al., "Treatment of nonunion of the tibia with a capacitively coupled electrical filed," *J. of Trauma*, 1984, 24 (2), 153-155.

Brighton, C.T., et al., "Tibial nonunion treated with direct current, capactitive coupling, or bone graft," *Clin. Of Orthop. And related Res.*, 1995, 321, 223-234.

Carter, E.L., et al., "Field distributions in vertebral bodies of the rat during electrical stimulation: a parametric study," *IEEE Trans. on Biomed. Eng.*, Mar. 1989, 36(3), 333-345.

Goodman, R., et al., "Exposure of salivary gland cells to low-frequency electromagnetic fields alters polypeptide synthesis," *Proc. Natl. Acad. Sci. USA*, Jun. 1988, 85, 3928-3932.

Goodwin, C.B., et al., "A double-blind study of capacitively coupled electrical stimulation as an adjunct to lumbar spinal fusions," *Spine*, 1999, 24(13), 1349-1356.

Grodzinsky, A.J., "Electromechanical and physicochemical properties of connective tissue," *Crit. Rev. Biomed. Engng.*, 1983, 9(2), 133-198.

Harrison, M.H.M., et al., "Use of pulsed electromagnetic fields in perthes disease: report of a pilot study," *J. Pediatr. Orthop.*, 1984, 4, 579-584.

Heermeier, K., et al., "Effects of extremely low frequency electromagnetic field (EMF) on collagen type 1mRNA expression and extracellular matrix synthesis of human osteoblatic cells," *Bioelectromagnietcs*, 1998, 19(4), 222-231.

Jiang, X., et al., "siRNA mediated inhibition of MMP-1 reduces invasive potential of a human chondrosarcoma cell line," *J. of Cellular Physiology*, 2005, 202, 723-730.

Jones, D.B., et al., "PEMF effects on differentiation and division in mirine melanoma cells are mediated indirectly through cAMP," *Trans. BRAGS 6*, 1986, 51.

Lorich, D.G., et al., "Biochemical pathway mediating the response of bone cells to capacitive coupling," *Clin. Orthop. and Related Res.*, 1998, 350, 246-256.

Massaro, L., et al., "Osteoarthritis of the knee joint: an eight year prospective study," *Ann Rheum Dis.*, 1989, 48, 893-897.

Mooney, V., "A randomized double-blind prospective study of the efficacy of pulsed electromagnetic fields for inter body lumbar fusions," *Spine*, 1990, 15(7), 708-712.

Norton, L.A., et al., "Pulsed electromagnetic fields alter phenotypic expression in chondroblasts in tissue culture," *J. Orthop. Res.*, 1988, 6, 685-689.

Pienkowski, D., et al., "Low-power electromagnetic stimulation of osteotomized rabbit fibuiae," *J. of Bone & Joint Surgery*, 1994, 76-A(4), 489-501.

Pezzetti, F., et al., "Effects of pulsed electromagnetic fields on human chondrocytes: and in vitro study," calcify Tissue Int., 1999, 65(5), 396-401.

Rodan, G.A., et al., "DNA synthesis in cartilage cells is stimulated by oscillating electric fields," *Science*, Feb. 10, 1978, 199, 690-692.

Ryaby, J.T., et al., "The effect of electromagnetic fields on protein phosphorylation and synthesis in murine melanoma cells," *BRAGS*, p. 32, (1986).

Ryaby, J.T., et al., "Pulsing electromagnetic fields affect the phosphorylation and expression of oncogene proteins," *Trans. BRAGS 6*, 1986, p. 78.

Wang, W., et al., "The increased level of PDGF-A constributes to the increased proliferation induced by mechanical stimulation in osteoblastic cells," *Biochem. And Molecular Biol. International*, Oct. 1997, 43(2), 339-346.

Wang, W., et al., "Up-regulation of chondrocyte matrix genes and products by electric fields," *Clin. Orthopaedics & Related Res.*, 2004, 427S, S163-S173.

Zhuang, H., et al., "Mechanical strain-induced proliferation of osteoblastic cells parallels increased TGF-β1 mRNA," *Biochem. Biophys. Res. Commun.*, 1996, 229, 449-453.

Zhuang, H., et al., "Electrical stimulation induces the level of TGF-β1 mRNA in osteoblastic cells by a mechanism involving calcium/calmodulin pathway," *Biochem. Biophys. Res. Commun.*, 1997, 237, 225-229.

* cited by examiner

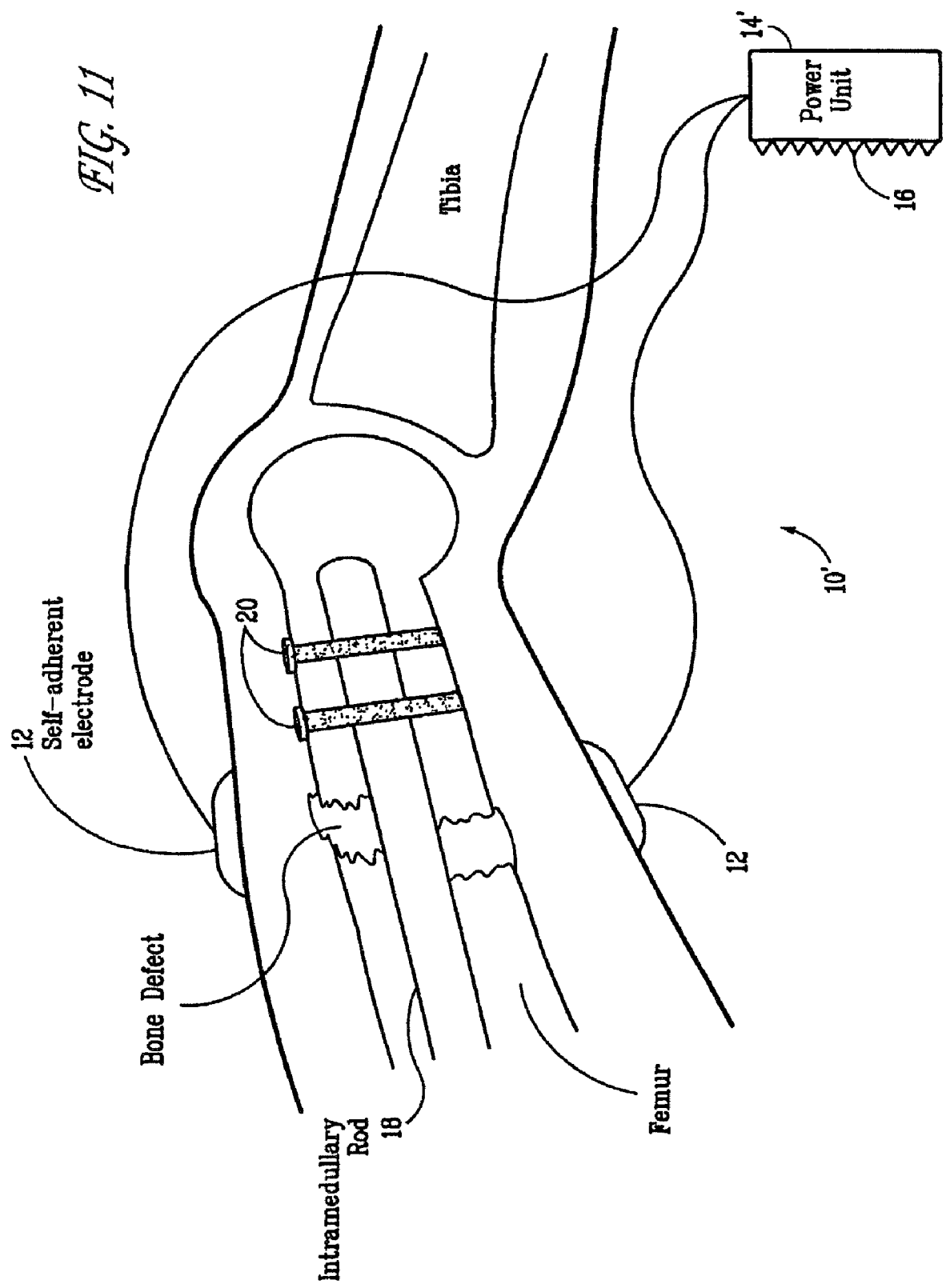

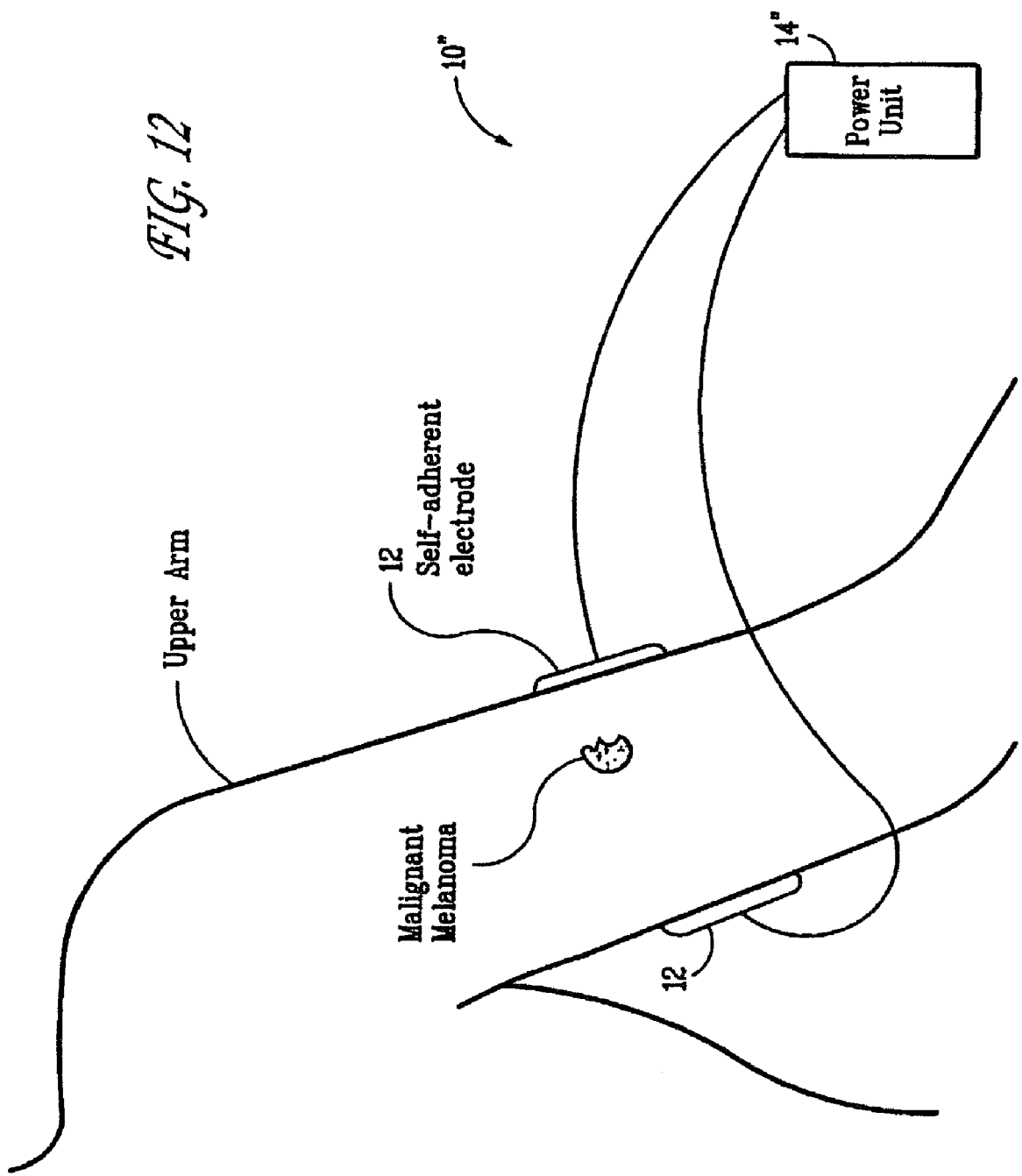

REGULATION OF GENES VIA APPLICATION OF SPECIFIC AND SELECTIVE ELECTRICAL AND ELECTROMAGNETIC SIGNALS

CROSS-REFERENCE TO RELATED APPLICATIONS

This application is a continuation of U.S. patent application Ser. No. 10/257,126 filed Oct. 8, 2002 which is a U.S. National Phase of PCT/US01/05991 filed Feb. 23, 2001, which claims priority to U.S. Provisional Application No. 60/184,491 filed Feb. 23, 2000.

FIELD OF THE INVENTION

The present invention is directed to methods of regulating gene expression in target cells via the application of specific and selective electric and electromagnetic signals to the target cells for the treatment of injured or diseased tissue, cartilage, or bone, as well as devices for generating the signals.

BACKGROUND OF THE INVENTION

The bioelectrical interactions and activity believed to be present in a variety of biological tissues and cells are one of the least understood of the physiological processes. However, there has recently been much research into these interactions and activity regarding the growth and repair of certain tissues and cells. In particular, there has been much research into stimulation by electric and electromagnetic fields and its effect on the growth and repair of bone and cartilage. Researchers believe that such research might be useful in the development of new treatments for a variety of medical problems.

Osteoarthritis, also known as degenerative joint disease, is characterized by degeneration of articular cartilage as well as proliferation and remodeling of subchondral bone. The usual symptoms are stiffness, limitation of motion, and pain. Osteoarthritis is the most common form of arthritis, and prevalence rates increase markedly with age. It has been shown that elderly patients with self-reported osteoarthritis visit doctors twice as frequently as their unaffected peers. Such patients also experience more days of restricted activity and bed confinement compared to others in their age group. In one study, the majority of symptomatic patients became significantly disabled during an 8-year follow-up period. Massardo et al., Ann Rheum Dis 48: 893-7 (1989).

Nonsteroidal anti-inflammatory drugs (NSAIDs) remain the primary treatment modality for osteoarthritis. It is unknown whether the efficacy of NSAIDs is dependent upon their analgesic or anti-inflammatory properties or the slowing of degenerative processes in the cartilage. There is also a concern that NSAIDs may be deleterious to patients. For example, NSAIDs have well known toxic effects in the stomach, gastrointestinal tract, liver and kidney. However, aspirin inhibits proteoglycan synthesis and normal cartilaginous repair processes in animals. One study in humans suggested that indomethacin might accelerate breakdown of hip cartilage. All adverse effects appear more commonly in the elderly—the very population most susceptible to osteoarthritis.

In the disease commonly known as osteoporosis, bone demineralizes and becomes abnormally rarefied. Bone comprises an organic component of cells and matrix as well as an inorganic or mineral component. The cells and matrix comprise a framework of collagenous fibers which is impregnated with the mineral component of calcium phosphate (85%) and calcium carbonate (10%) which imparts rigidity to the bone. While osteoporosis is generally thought as afflicting the elderly, certain types of osteoporosis may affect persons of all ages whose bones are not subject to functional stress. In such cases, patients may experience a significant loss of cortical and cancellous bone during prolonged periods of immobilization. Elderly patients are known to experience bone loss due to disuse when immobilized after fracture of a bone, which may ultimately lead to a secondary fracture in an already osteoporotic skeleton. Diminished bone density may lead to vertebrae collapse, fractures of hips, lower arms, wrists, ankles as well as incapacitating pains. Alternative nonsurgical therapies for such diseases are needed.

Pulsed electromagnetic fields (PEMF) and capacitive coupling (CC) have been used widely to treat nonhealing fractures and related problems in bone healing since approval by the Food and Drug Administration in 1979. The original basis for the trial of this form of therapy was the observation that physical stress on bone causes the appearance of tiny electric currents that, along with mechanical strain, were thought to be the mechanisms underlying transduction of the physical stresses into a signal that promotes bone formation. Along with direct electric field stimulation that was successful in the treatment of nonunion, noninvasive technologies using PEMF and capacitive coupling (where the electrodes are placed on the skin in the treatment zone) were also found to be effective. Pulsed electromagnetic fields generate small induced currents (Faraday currents) in the highly conductive extracellular fluid, while capacitive coupling directly causes currents in the tissues; both PEMFs and CC thereby mimic endogeneous electrical currents.

The endogeneous electrical currents, originally thought to be due to phenomena occurring at the surface of crystals in the bone, have been shown to be due primarily to movement of fluid containing electrolytes in channels of the bone containing organic constituents with fixed negative charges, generating what are called "streaming potentials." Studies of electrical phenomena in cartilage have demonstrated a mechanical-electrical transduction mechanism that resembles those described in bone, appearing when cartilage is mechanically compressed, causing movement of fluid and electrolytes over the surface of fixed negative charges in the proteoglycans and collagen in the cartilage matrix. These streaming potentials apparently serve a purpose in cartilage similar to that in bone, and, along with mechanical strain, lead to signal transduction that is capable of stimulating chondrocyte synthesis of matrix components.

The main application of direct current, capacitive coupling, and PEMFs has been in orthopedics in healing of nonunion bone fractures (Brighton et al., *J. Bone and Joint Surgery,* 63: 2-13, 1981; Brighton and Pollack, *J. Bone and Joint Surgery,* 67: 577-585, 1985; Bassett et al., *Crit. Rev. Biomed. Eng.,* 17: 451-529 (1989); Bassett et al., *J AMA* 247: 623-8 (1982). Clinical responses have been reported in avascular necrosis of hips in adults and Legg-Perthes's disease in children. Bassett et al., *Clin Orthop* 246: 172-6 (1989); Aaron et al., *Clin Orthop* 249: 209-18 (1989); Harrison et al, *J Pediatr Orthop* 4: 579-84 (1984). It has also been shown that PEMFs (Mooney, Spine, 15: 708-712, 1990) and capacitive coupling (Goodwin, Brighton et al., *Spine,* 24: 1349-1356, 1999) can significantly increase the success rate of lumbar fusions. There are also reports of augmentation of peripheral nerve regeneration and function and promotion of angiogenesis. Bassett, *Bioassays* 6: 36-42 (1987). Patients with persistent rotator cuff tendinitis refractory to steroid injection and other conventional measures, showed significant benefit compared with placebo treated patients. Binder et al., Lancet 695-8

(1984). Finally, Brighton et al. have shown in rats the ability of an appropriate capacitive coupling signal to both prevent and reverse vertebral osteoporosis in the lumbar spine (Brighton et al., *J. Orthop. Res.* 6: 676-684, 1988; Brighton et al., *J Bone and Joint Surgery*, 71: 228-236, 1989).

More recently, research in this area has focused on the effects stimulation has on tissues and cells. For example, it has been conjectured that direct currents do not penetrate cellular membranes and that control is achieved via extracellular matrix differentiation. Grodzinsky, *Crit. Rev. Biomed. Engng* 9:133 (1983). In contrast to direct currents, it has been reported that PEMFs can penetrate cell membranes and either stimulate them or directly affect intracellular organelles. An examination of the effect of PEMFs on extracellular matrices and in vivo endochondral ossification found increased synthesis of cartilage molecules and maturation of bone trabeculae. Aaron et al., *J. Bone Miner. Res.* 4: 227-233 (1989). More recently, Lorich, Brighton et al. reported (*Clin Orthop and Related Research* 350: 246-256, 1998) that signal transduction of a capacitively coupled signal is via voltage gated calcium channels, leading to an increase in cytosolic calcium with a subsequent increase in activated (cytoskeletal) calmodulin.

Much research has been directed at studying tissue culture in order to understand the mechanisms of response. In one study, it was found that electric fields increased [$^3$H]-thymidine incorporation into the DNA of chondrocytes, supporting the notion that Na and $Ca^{2+}$ fluxes generated by electrical stimulation trigger DNA synthesis. Rodan et al., *Science* 199: 690-692 (1978). Studies have found changes in the second messenger, cAMP, and cytoskeletal rearrangements due to electrical perturbations. Ryaby et al., *Trans. BRAGS* 6: (1986); Jones et al., *Trans. BRAGS* 6: 51 (1986); Brighton and Townsend, *J. Orthop. Res.* 6: 552-558, 1988. Other studies have found effects on glycosaminoglycan, sulphation, hyaluronic acid, lysozyme activity and polypeptide sequences. Norton et al., *J. Orthop. Res.* 6: 685-689 (1988); Goodman et al., *Proc. Natn. Acad. Sci.* USA 85: 3928-3932 (1988).

It was reported in 1996 by the present inventors that a cyclic biaxial 0.17% mechanical strain produces a significant increase in TGF-$\beta_1$ mRNA in cultured MC3T3-E1 bone cells. Brighton et al., *Biochem. Biophys. Res. Commun.* 229: 449-453 (1996). Several significant studies followed in 1997. In one study it was reported that the same cyclic biaxial 0.17% mechanical strain produced a significant increase in PDGF-A mRNA in similar bone cells. Brighton et al., *Biochem. Biophys. Res. Commun.* 43: 339-346 (1997). It was also reported that a 60 kHz capacitively coupled electric field of 20 mV/cm produced a significant increase in TGF-$\beta_1$ in similar bone cells. Brighton et al., *Biochem. Biophys. Res. Commun.* 237: 225-229 (1997). However, the effect such a field would have on other genes has not been reported in the literature.

There is a great need for methods and devices for the treatment of diseased or injured tissue, bones, and cartilage, as well as disease states such as osteoarthritis, osteoporosis, and cancer. In particular, there is a need for methods and devices for the treatment of diseased or injured bone, tissue, and cartilage cells and for the treatment of such disease states by selectively up-regulating or down-regulating certain genes. The present invention is directed to these, as well as other, important needs in the art.

SUMMARY OF THE INVENTION

The present invention relates to regulating the gene expression of target cells via the application of specific and selective electric and/or electromagnetic signals. In particular, the present invention relates to methods of regulating the expression of genes via the application of such signals to target cells.

In a preferred embodiment of the invention, methods are provided for treating injured or diseased tissue, cartilage and/or bone by providing specific and selective electric and/or electromagnetic signals and exposing the injured or diseased tissue, cartilage and/or bone to the signals so as to regulate gene expression. In accordance with the method of the invention, a "specific and selective" signal is a signal that has predetermined characteristics of amplitude, duration, duty-cycle, frequency, and waveform that up-regulate or down-regulate a targeted gene or targeted functionally complementary genes (specificity). This allows one to choose different signals to up-regulate or down-regulate various gene expressions in order to achieve a given biological or therapeutic response (selectivity). The invention further relates to devices employing the methods described herein to generate specific and selective signals that up-regulate and/or down-regulate the target gene(s).

In related aspects, the present invention relates to methods and devices for the treatment of bone defects, osteoarthritis, osteoporosis, cancer, and other diseases. The method of the invention also includes the methodology for determining the "specific and selective" signal for a particular target gene by methodically varying the duration of a starting signal known to increase or suspected to increase cellular production of a given protein. After selecting the optimal duration, the amplitude of the signal is varied for the optimal duration of time as determined by the gene expression of the protein of interest. The duty cycle, frequency, and waveform are varied methodically while keeping the other signal characteristics constant. This process is repeated until the optimal signal is determined that produces the greatest increase in the gene expression of the protein of interest.

These and other aspects of the present invention will be elucidated in the following detailed description of the invention.

BRIEF DESCRIPTION OF THE DRAWINGS

The present invention will be apparent from the following detailed description of the invention taken in conjunction with the accompanying drawings, of which:

FIG. 11 is a diagram illustrating a nonunion of the femur stabilized by an intramedullary rod that is locked by two transcortical screws, and a device for the treatment of bone defects, in accordance with preferred embodiments of the present invention.

FIG. 12 is a diagram illustrating a device for the treatment of malignant melanoma, in accordance with preferred embodiments of the present invention.

DETAILED DESCRIPTION OF ILLUSTRATIVE EMBODIMENTS

Figure 1:
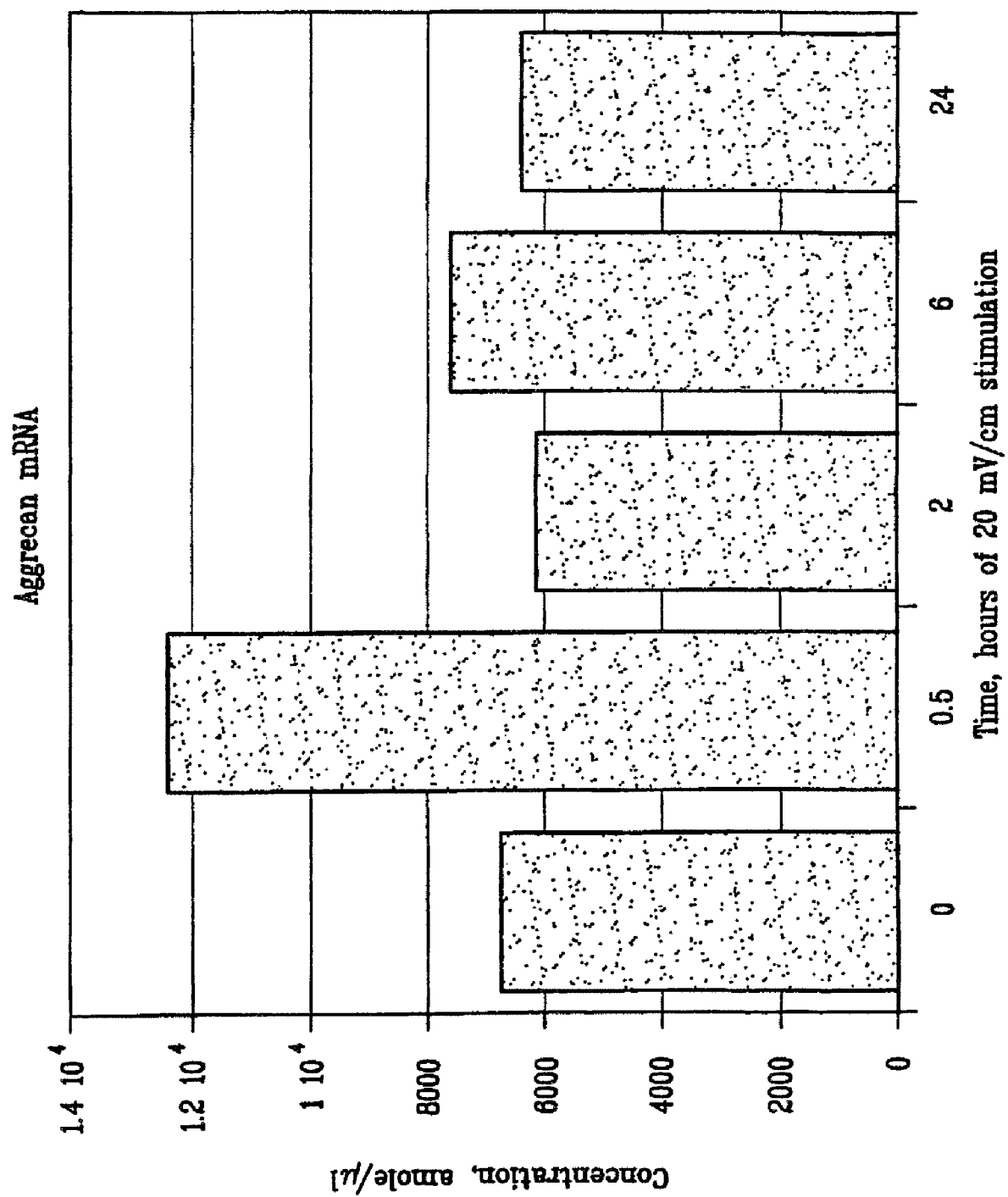
FIG. 1 is a graphic representation of aggrecan mRNA production by articular cartilage chondrocytes stimulated with a 20 mV/cm capacitively coupled electric field for various time durations. In this example, the response is time duration specific.

Preferred embodiments of the invention will be described in detail below with reference to FIGS. 1-12. Those skilled in the art will appreciate that the description given herein with respect to those figures is for exemplary purposes only and is not intended in any way to limit the scope of the invention. All questions regarding the scope of the invention may be resolved by referring to the appended claims.

The present invention is based on the discovery that the expression of certain genes can be regulated by the application of specific and selective electric and/or electromagnetic signals. In other words, it has been discovered by the present inventors that there is a specific electric and/or electromagnetic signal for regulating each gene in bone, cartilage and other tissue cells and that these specific signals are capable of specifically and selectively regulating the genes in such cells. In particular, gene expression governing the growth, maintenance, repair, and degeneration or deterioration of tissues or cells can be regulated in accordance with the invention via the application of specific and selective electric and /or electromagnetic signals so as to produce a salutary clinical effect. Such discoveries are useful in the development of treatment methods that target certain medical conditions including bone fractures and defects, osteoarthritis, osteoporosis, cancer and other diseases, as well as for developing devices employing such methods.

As used herein, the phrase "signal" is used to refer to a variety of signals including mechanical signals, ultrasound signals, electromagnetic fields and electric fields. It is to be understood that the phrase "signal" may refer to an electrical field whether it is a combined field or a pulsed electromagnetic field or generated by direct current, capacitive coupling or inductive coupling.

The phrase "remote" is used to mean acting, acted on or controlled from a distance. "Remote" regulation refers to controlling the expression of a gene from a distance. To provide "remotely" refers to providing from a distance. For example, providing a specific and selective signal from a remote source can refer to providing the signal from a source at a distance from tissue or a cell or from a source outside of or external to the body.

The phrase "specific and selective" signal means a signal that has predetermined characteristics of amplitude, duration, duty-cycle, frequency, and waveform that up-regulate or down-regulate a targeted gene or targeted functionally complementary genes (specificity). This allows one to choose different signals to up-regulate or down-regulate various gene expressions in order to achieve a given biological or therapeutic response (selectivity).

The term "regulate" means to control gene expression. Regulate is understood to include both up-regulate and down-regulate, Up-regulate means to increase expression of a gene, while down-regulate means to inhibit or prevent expression of a gene.

"Functionally complementary" refers to two or more genes whose expressions are complementary or synergistic in a given cell or tissue.

"Tissue" refers to an aggregate of cells together with their extracellular substances that form one of the structural materials of a patient. As used herein, the term "tissue" is intended to include muscle and organ tissue as well as bone or cartilage tissue. Also, the term "tissue" as used herein may also refer to an individual cell.

"Patient" refers to an animal, preferably a mammal, more preferably a human.

The present invention provides treatment methods and devices that target certain tissues, cells or diseases. In particular, the gene expression associated with the repair process in injured or diseased tissues or cells can be regulated by the application of electric signals that are specific and selective for the genes to be regulated in the target tissues or cells. Gene expression can be up-regulated or down-regulated by the application of signals that are specific and selective for each gene or each set of complementary genes so as to produce a beneficial clinical effect. For example, a particular specific and selective signal may up-regulate a certain desirable gene expression, while the same or another particular specific and selective signal may down-regulate a certain undesirable gene expression. A certain gene may be up-regulated by one particular specific and selective signal and down-regulated by another specific and selective signal. Those skilled in the art will understand that certain diseased or injured tissues can be targeted for treatment by regulating those genes governing the growth, maintenance, repair, and degeneration or deterioration of the tissues.

The methods and devices of the present invention are based on identifying those signals that are specific and selective for the gene expression associated with certain targeted diseased or injured tissue. For example, electricity in its various forms (e.g., capacitive coupling, inductive coupling, and combined fields) can specifically and selectively regulate gene expression in targeted tissues or cells in a patient's body by varying the frequency, amplitude, waveform or duty cycle of the applied signal for each selected gene. The duration of time exposed to electricity can also influence the capability of electricity to specifically and selectively regulate gene expression in targeted tissues or cells in a patient's body. Specific and selective signals may be applied to each gene systematically until the proper combination of frequency, amplitude, waveform, duty cycle, and duration is found that provides the desired effect on gene expression.

It is to be understood that a variety of diseased or injured tissues or disease states can be targeted for treatment because the specificity and selectivity of an electric field for a certain gene expression can be influenced by several factors. In particular, an electrical field of appropriate frequency, amplitude, waveform and/or duty cycle can be specific and selective for the expression of certain genes and thus provide for targeted treatments. Temporal factors (e.g., duration of time exposed to the electrical field) can also influence the specificity and selectivity of an electric field for a particular gene expression, the regulation of gene expression may be more effective (or made possible) via the application of an electrical field for a particular duration of time. Therefore, those skilled in the art will understand that the present invention provides for varying the frequency, amplitude, waveform, duty cycle and/or duration of application of an electric field until the electric field is found to be specific and selective for certain gene expressions in order to provide for treatments targeting a variety of diseased or injured tissue or diseases.

Thus, the present invention can provide for targeted treatments because it is possible to regulate expression of certain genes associated with a particular diseased or injured tissue via the application of specific and selective signals including electric fields of appropriate frequency, amplitude, waveform and/or duty cycle for an appropriate duration of time. The specificity and selectivity of a signal including an electrical field may thus be influenced so as to regulate the expression of certain genes in order to target certain diseased or injured tissue or disease states for treatment. The present invention thereby provides for a multitude of targeted treatments including the treatment of bone defects, osteoarthritis, osteoporosis and cancer.

The present invention further provides devices for the treatment of injured or diseased tissue as well as certain disease states. In particular, the present invention provides devices that include a source of at least one signal specific and selective for a certain gene expression. The devices of the present invention can provide for the production of such signals for application to the targeted cells by at least one electrode adapted to apply the specific and selective signal.

Figure 10:
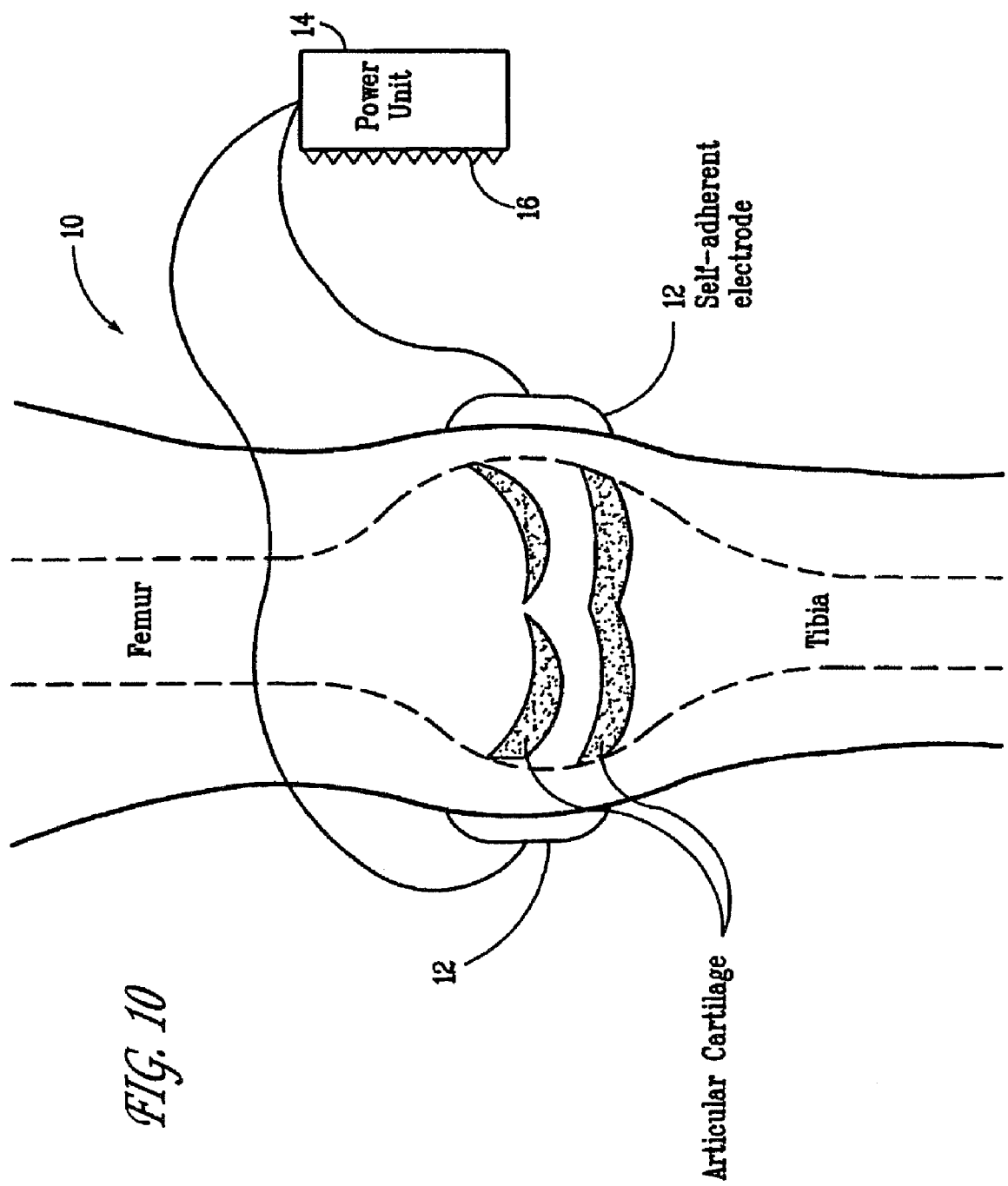
FIG. 10 is a diagram illustrating a device for the treatment of osteoarthritis of the knee, in accordance with preferred embodiments of the present invention.

The devices of the present invention are capable of applying specific and selective signals directly to diseased or injured tissue and/or to the skin of a patient. The devices of the present invention may also provide for the remote application of specific and selective signals (e.g., application of a signal at a distance from diseased or injured tissue), although it will be appreciated that capacitively coupled devices must touch the subject's skin. The devices of the present invention may include means for attaching the electrodes to the body of a patient in the vicinity of injured or diseased tissue. For example, self-adherent conductive electrodes may be attached to the skin of the patient on both sides of a knee joint afflicted with osteoporosis as shown in FIG. 10. As also shown in FIG. 10, the devices of the present invention may also include means for attaching the device to the body of a patient. For example, the devices of the present invention may include electrodes attached to a power unit which has a Velcro patch on the reverse side such that the power unit can be attached to a Velcro strap fitted around the calf, thigh or waist.

The devices of the present invention can be employed in a variety of ways. The devices of the present invention may be portable or may be temporarily or permanently attached to a patient's body. The devices of the present invention are preferably non-invasive. For example, the devices of the present invention may be applied to the skin of a patient by application of electrodes adapted for contact with the skin of a patient for the application of predetermined specific and selective signals. Such signals may also be applied via coils in which time varying currents flow, thus producing specific and selective electromagnetic fields which penetrate the tissue. The devices of the present invention may also be capable of implantation in a patient, including implantation under the skin of a patient.

Examples below will illustrate that the methods of the present invention may provide for bone growth and repair via regulation of gene expression in bone cells. The methods of the present invention can stimulate bone growth and repair in the vicinity of fresh fractures and non-union fractures. Bone growth and repair also can be stimulated in the vicinity of osteoarthritis or osteoporosis. A variety of cells can be targeted by the methods of the present invention including bone cells, cartilage cells, fibrous tissue cells, stem cells, and cancer cells.

Examples below also will illustrate that the methods of the present invention may provide for cartilage growth and repair. Cartilage growth and repair can be stimulated via signals specific and selective for the expression of certain genes. For example, the methods of the present invention can stimulate articular cartilage repair in osteoarthritis patients and provide for the regulation of gene expression in cartilage cells. In particular, the methods of the present invention can provide for the up-regulation of genes that repair cartilage (e.g., genes encoding for aggrecan and Type II collagen), down-regulation of genes that destroy cartilage (e.g., genes encoding for metalloproteinase) and the up-regulation of genes that inhibit metalloproteinases that destroy articular cartilage (e.g., genes encoding for tissue inhibitors of metalloproteinase). A variety of cartilage cells can be targeted by the methods of the present invention including articular chondrocytes and including articular cartilage, hyaline cartilage, and growth plate cartilage.

The examples below further illustrate that the methods of the present invention provide for the regulation of gene expression in articular chondrocytes. For example, in the examples below, fetal articular chondrocytes have been exposed to a capacitively coupled 60 kHz electrical field of 20 mV/cm for 0.5, 2.0, 6.0 and 24.0 hours. A statistically significant incorporation of $^{35}SO_4$/ugDNA (indicating significant proteoglycan synthesis) was found after only 0.5 hours of stimulation. An identical experiment was repeated and the levels of aggrecan mRNA, the messenger for the major cartilage proteoglycan, monitored. After only 0.5 hours of electrical stimulation there was a significant increase (almost 100%) in aggrecan mRNA. Accordingly, temporal factors may influence the specificity and selectivity of a signal regulating gene expression in articular chondrocytes.

The methods of the present invention also provide for the treatment of certain diseases. In particular, the methods of the present invention can provide for the treatment of cancer. In a patient with a primary (or even metastatic) cancer, metalloproteinase is at least partly responsible for spread of the cancer. Metalloproteinase enzymatically breaks down fibrous walls or membranes erected by adjacent cells in an attempt to contain the cancer. However, as mentioned above, tissue inhibitors of metalloproteinase may inhibit the production of such metalloproteinases. Accordingly, methods of the present invention can provide for the down-regulation of genes encoding for metalloproteinase and the up-regulation of genes encoding for tissue inhibitors of metalloproteinase ("TIMP"). Those skilled in the art will understand that a variety of other diseases may be targeted for treatment via the methods of the present invention.

Figure 5:
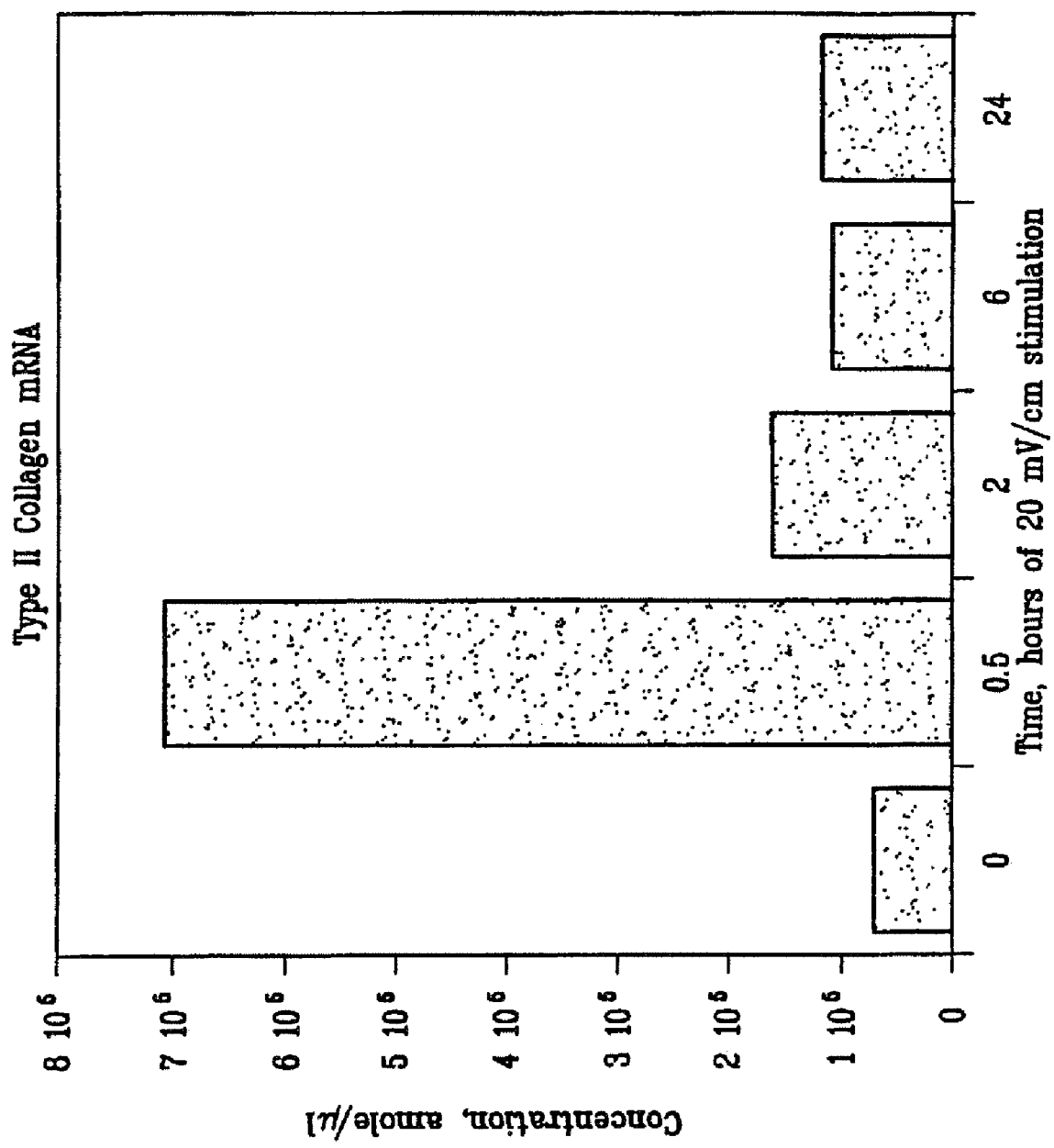
FIG. 5 is a graphic representation of Type TI collagen mRNA production in articular cartilage chondrocytes stimulated by a 20 mV/cm capacitively coupled electric field for various time durations. In this example, the response is time duration specific, similar to that of the complimentary aggrecan mRNA.

While not limiting the present invention in any way, it is presently believed that those genes that are functionally complementary may respond to identical or substantially similar signals. In other words, a signal may be specific and selective for functionally complementary genes. With reference to FIGS. 1 and 5, and as described below with respect to examples 1 and 2, those genes encoding aggrecan and Type II collagen can both be regulated by a 20 mV/cm, 60 kHz capacitively coupled signal. Each of these genes regulates cartilage matrix formation and is thus believed to be functionally complementary. On the other hand, as described below with respect to example 5, a 20 mV/cm, 60 kHz capacitively coupled signal regulates the gene expression for encoding TGF-β, but does not regulate the gene expression for PDGF-A. Each of these genes participates in the regulation of different phases and physiologic processes of bone healing and are thus are not believed to be functionally complementary.

FIGS. 10-12 provide examples of the devices of the present invention. The devices of the present invention can include a source of specific and selective signals, a power unit and at least one electrode. The devices of the present invention can be portable. For example, the electrodes may be attached to a power unit can be attached to a Velcro strap which can be fitted around the calf, thigh or waist. Such a device can be used to apply, e.g., a specific and selective electric field for 30 minutes or more per day so as to up-regulate the gene expression of, e.g., aggrecan or Type II collagen.

Those skilled in the art will understand that the devices of the present invention can be provided in a variety of forms including a capacitively coupled power unit with programmed multiple switchable specific and selective signals for application to one pair or to multiple pairs of electrodes, electromagnetic coils attached to a power unit with switchable multiple specific and selective signals, and an ultrasound stimulator with a power supply for generating specific and selective signals. Generally speaking, device preference is based on patient acceptance and patient compliance. The smallest and most portable unit available in the art at the present time is a capacitive coupling unit; however, patients with extremely sensitive skin may prefer to use inductive coupling units. On the other hand, ultrasound units require the most patient cooperation but may be desirable for use by certain patients.

EXAMPLES

The invention is further demonstrated in the following examples, which are for purposes of illustration, and are not intended to limit the scope of the present invention.

Materials and Methods

Chondrocyte cultures were prepared from fetal bovine articular cartilage.

Chondrocytes ($5 \times 10^5$ cells/cm$^2$) were plated onto specially modified Cooper dishes. The cells were grown to seven days with the medium changed just prior to beginning of the experimental condition. The experimental cell cultures throughout these studies were subjected to a capacitively coupled 60 kHz sine wave signal electric field with an output of 44.81 volts peak to peak. This produced a calculated-field strength in the culture medium in the dishes of 20 mV/cm with a current density of 300 µA/cm$^2$. Control cell culture dishes were identical to that of the stimulated dishes except that the electrodes were not connected to a function generator.

Total RNA was isolated using TRIzol, according to the manufacturer's instructions, and reversed transcription using SuperScript II reverse transcriptase was performed. Oligonucleotide primers to be used in the competitive PCR technique were selected from published cDNA sequences. Quantitative analysis of PCR products was performed using ScionImage software.

The optimal signal for the desired gene regulation was found systematically as follows. An electrical signal known to increase (or even just suspected to increase) cellular production of a given protein is taken as the starting signal for determining the specific signal for the gene expression (mRNA) of that protein. A dose-response curve is first performed by varying the duration of the signal while holding all the other signal characteristics constant (amplitude, duty-cycle, frequency, and waveform). This determines the optimal duration of the starting signal for the gene expression of that protein. A second dose-response curve is performed by varying the amplitude for the optimal duration of time. This determines the optimal amplitude for the optimal duration of time as determined by the gene expression of the protein of interest. A third dose-response curve is then performed, this time varying the duty-cycle from 100% (constant) to 1% or less while holding the optimal amplitude and other signal characteristics constant. A dose-response is repeated a fourth time (varying frequency) and a fifth time (varying waveform) each time keeping the other signal characteristics constant. By this method an optimal signal is determined for producing the greatest increase in the gene expression of the protein of interest.

Protein expression may be determined by any method known in the art, such as reverse transcriptase PCR, Northern analysis, immunoassays, and the like.

Example 1

Aggrecan Production By Articular Chondrocytes

Articular chondrocytes were exposed to a capacitively coupled electric signal of 20 mV/cm at 60 kHz. The results are illustrated in FIGS. 1-4.

FIG. 1 is a graphic representation of aggrecan mRNA production by articular cartilage chondrocytes (attomole per µl) stimulated with a 20 mV/cm capacitively coupled electric field for time durations of 0 (control), 0.5, 2, 6, and 24 hours. In this example, 30 minutes stimulation was found to provide a significant increase (almost a two-fold increase) in aggrecan mRNA. The response is thus time duration specific.

Figure 2:
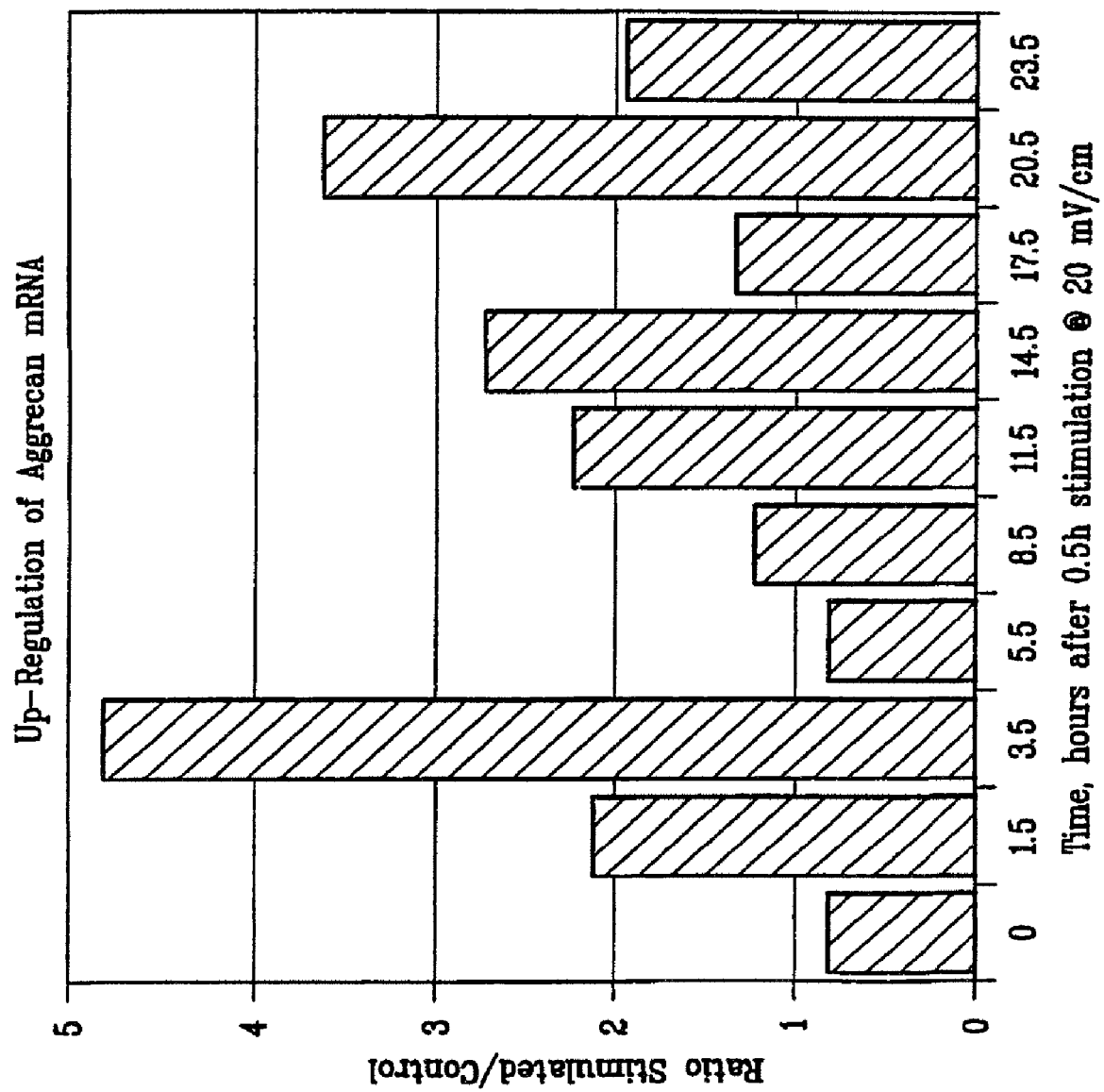
FIG. 2 is a graphic representation of the duration and magnitude of aggrecan mRNA up-regulation in articular cartilage chondrocytes following 30 minutes stimulation with a 20 mV/cm capacitively coupled electric field.
Figure 3:
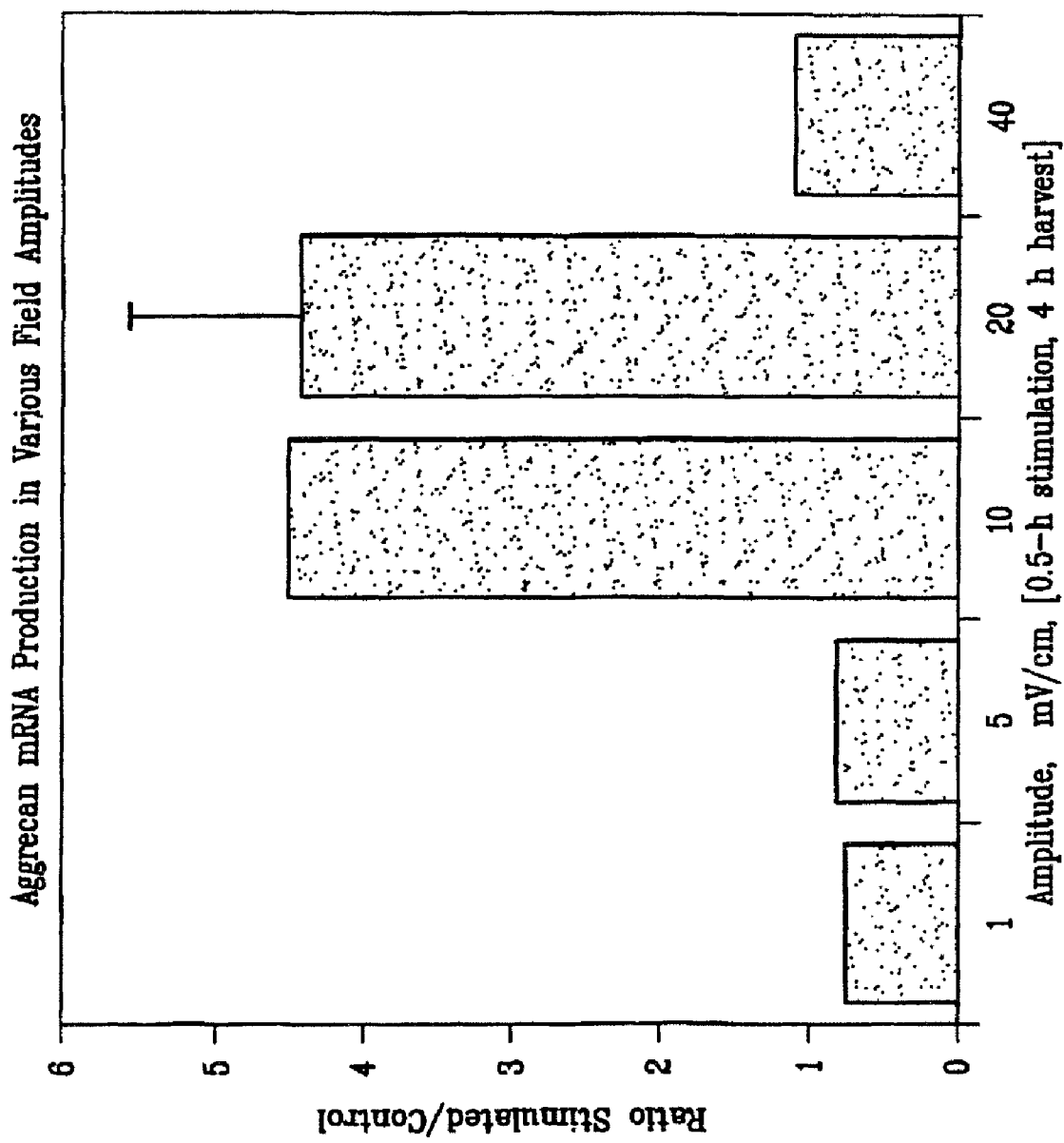
FIG. 3 is a graphic representation of aggrecan mRNA production in articular cartilage chondrocytes stimulated by various capacitively coupled electric field amplitudes, all for 30 minutes duration. In this example, the response is electric field amplitude specific.

FIG. 2 is a graphic representation of the duration and magnitude of aggrecan mRNA up-regulation in articular cartilage chondrocytes following 30 minutes stimulation with a 20 mV/cm (60 kHz) capacitively coupled electric field. As illustrated, it was found that the peak up-regulation occurs 3½ hours following the cessation of the 30 minute stimulation period. FIG. 2 also illustrates that the up-regulation is cyclic, with secondary, smaller peaks of up-regulation occurring 14½ hours and 20½ hours after cessation of the 30 minute stimulation period FIG. 3 is a graphic representation of aggrecan mRNA production in articular cartilage chondrocytes stimulated by various capacitively coupled electric field amplitudes, all for 30 minutes duration. In this example, 10-20 mV/cm showed significant increases in aggrecan mRNA production. Thus, the response is electric field amplitude specific.

Figure 4:
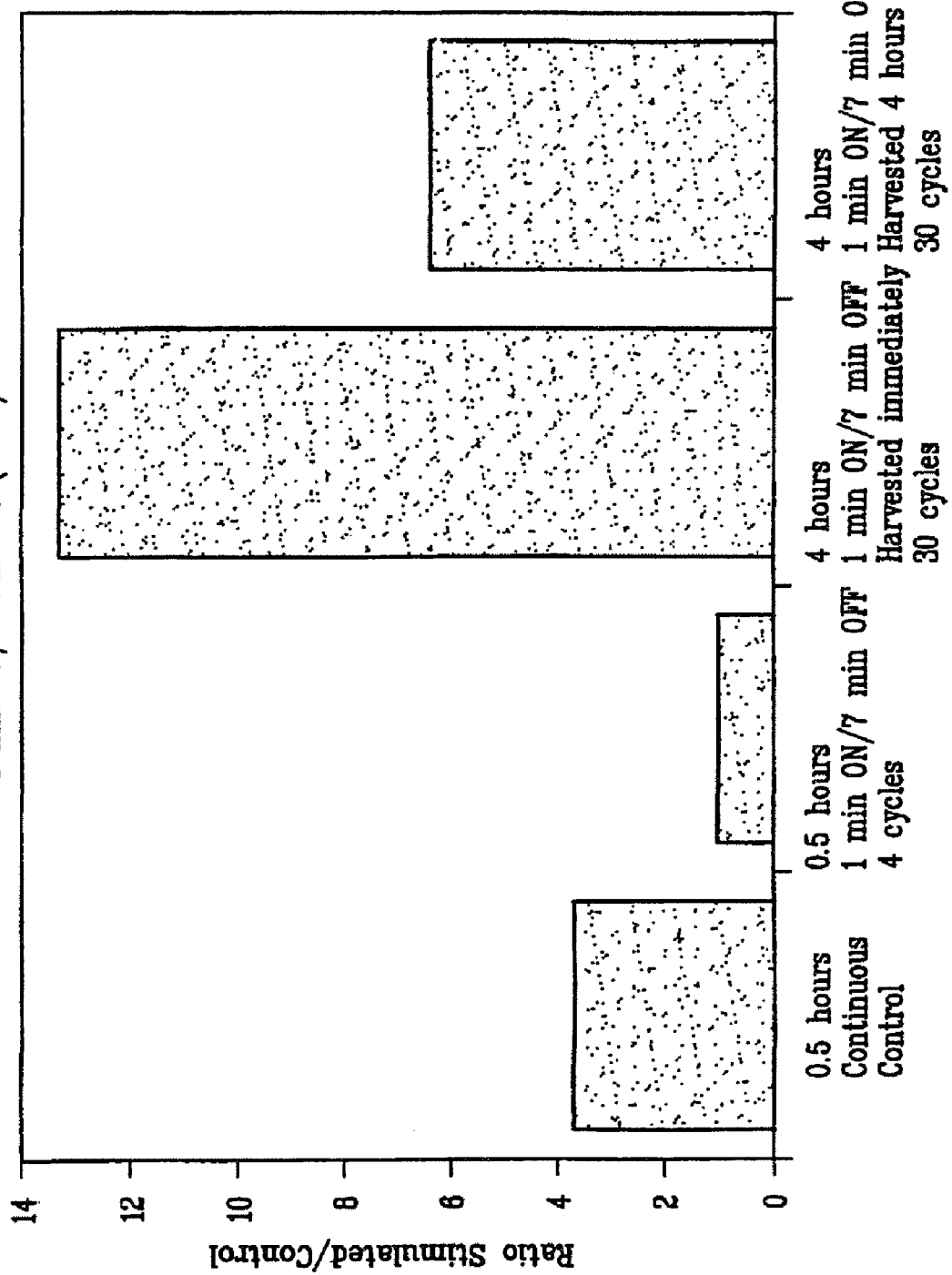
FIG. 4 is a graphic representation of aggrecan mRNA production in articular cartilage chondrocytes stimulated by 20 mV/cm capacitively coupled electric field using various duty cycles. In this example, the response is duty cycle specific, and the duty cycle is time-wise selective.

FIG. 4 is a graphic representation of aggrecan mRNA production in articular cartilage chondrocytes stimulated by 20 mV/cm (60 kHz) capacitively coupled electric field using various duty cycles. As illustrated, a duty cycle of 1 minute on/7 minutes off (12/5% duty cycle) pulsed for 30 cycles (total "on" time of stimulation =30 minutes) leads to a far greater production of aggrecan mRNA than 30 minutes of constant (control, 100% duty cycle) stimulation. The response is thus duty cycle specific. FIG. 4 also illustrates that a 1 minute on/7 minute off (12.5% duty cycle) signal for 4 hours gives significantly more aggrecan mRNA than does the same 12.5% duty cycle applied for 30 minutes. The duty cycle is thus time-wise selective.

Example 2

Type II Collagen Production By Articular Chondrocytes

Articular chondrocytes were exposed to a capacitively coupled electric signal of 20 mV/cm at 60 kHz. The results are illustrated in FIGS. 5-7.

FIG. 5 is a graphic representation of Type TI collagen mRNA production (attomole per μl) in articular chondrocytes stimulated by a 20 mV/cm (60 kHz) capacitively coupled electric field for time durations of 0 (control), 0.5,2,6 and 24 hours. In this example, 30 minutes of stimulation provided a significant increase (approximately ten-fold increase) in collagen Type II mRNA. This shows that the response is time duration specific, similar to that of the complementary aggrecan mRNA of Example 1.

Figure 6:
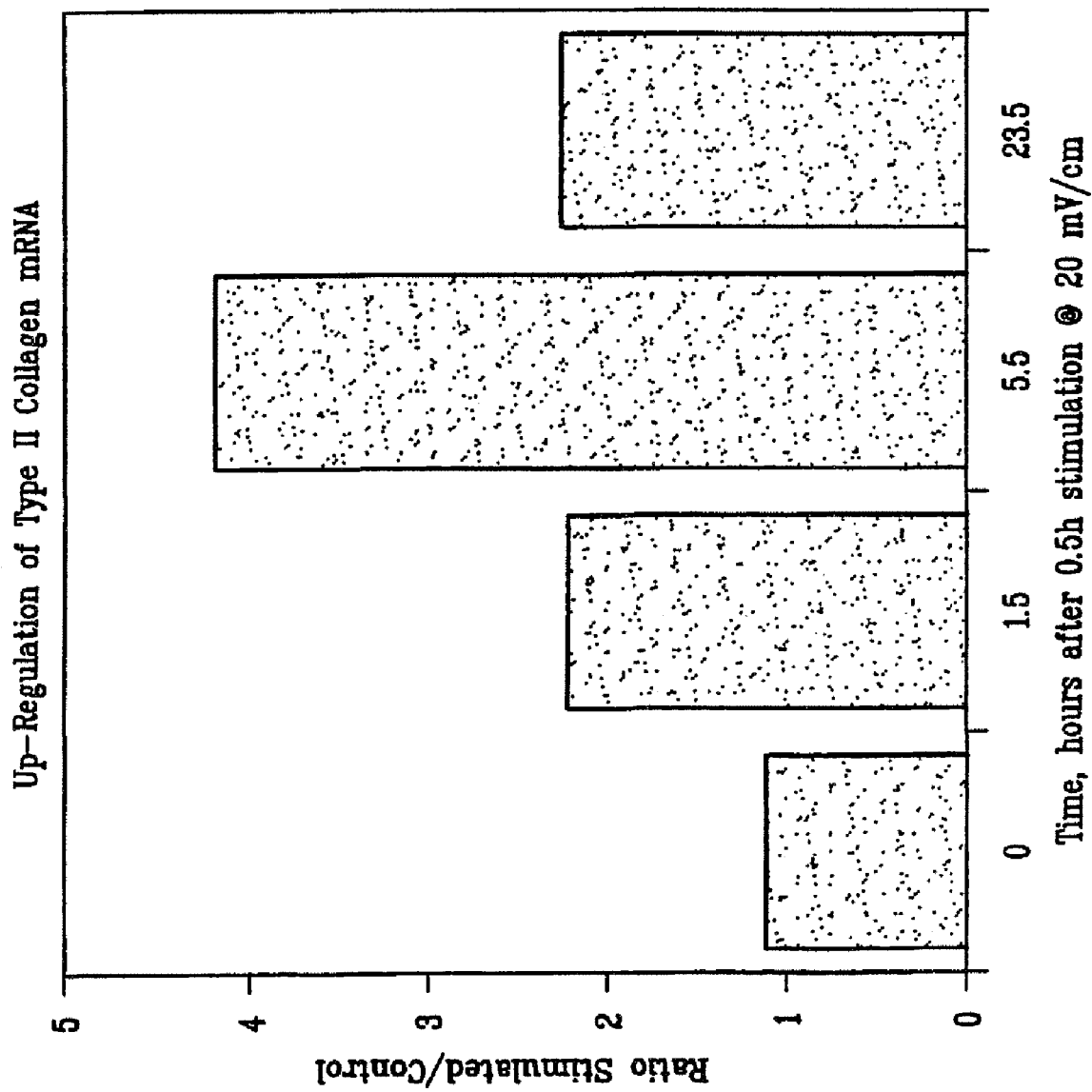
FIG. 6 is a graphic representation of the duration and magnitude of Type II collagen mRNA up-regulation in articular cartilage chondrocytes following 30 minutes stimulation with a 20 mV/cm capacitively coupled electric field.

FIG. 6 is a graphic representation of the duration and magnitude of Type II collagen mRNA up-regulation in articular chondrocytes following 30 minutes stimulation with a 20 mV/cm capacitively coupled electric field. FIG. 6 illustrates that peak up-regulation occurs 5% hours following cessation of the 30 minute stimulation period. It is noteworthy that aggrecan mRNA a complementary gene, reached a maximum production of aggrecan mRNA at 3½ hours after cessation of stimulation, 2 hours earlier than with Type II collagen mRNA (FIG. 2).

Figure 7:
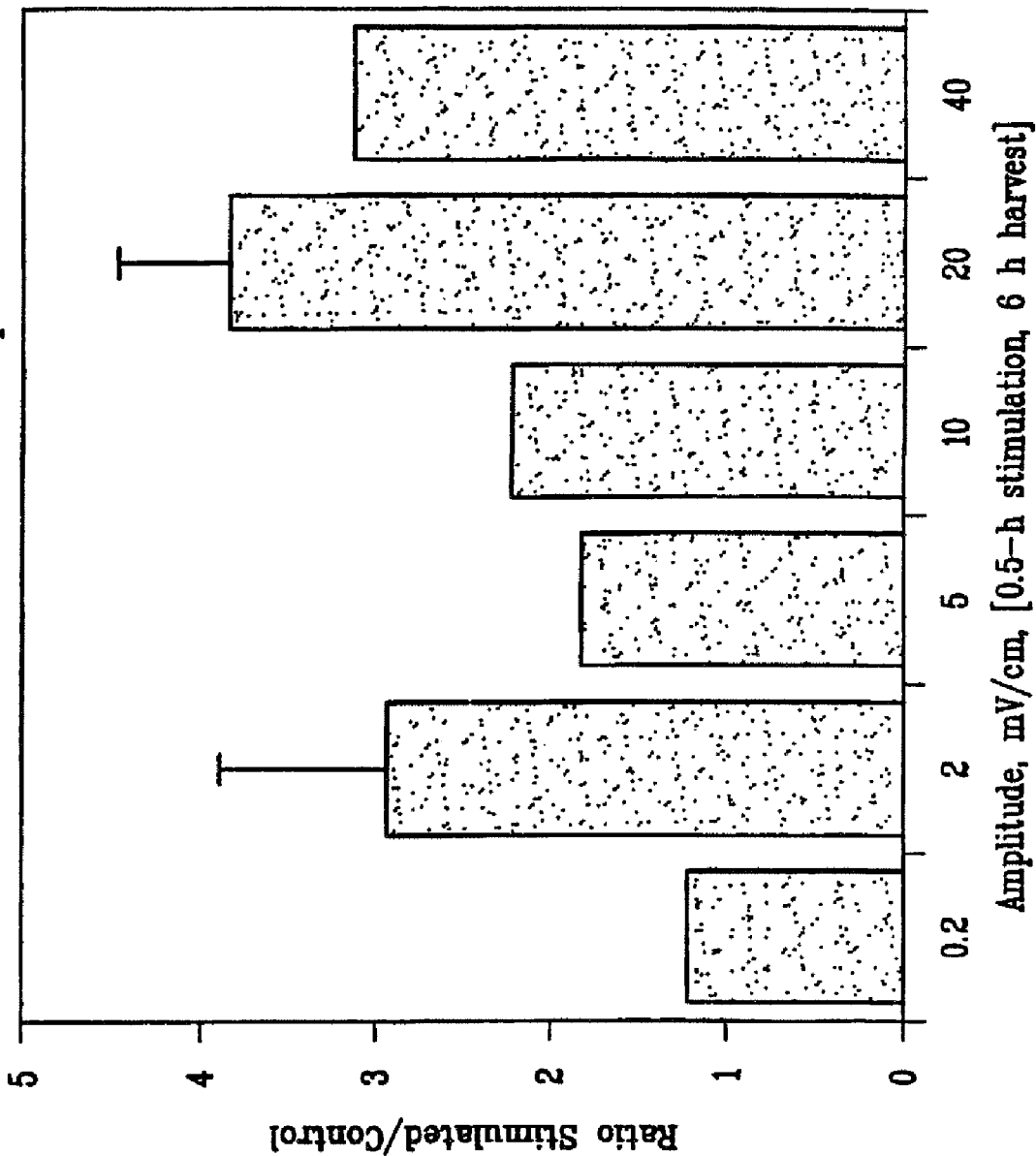
FIG. 7 is a graphic representation of Type II collagen mRNA production in articular cartilage chondrocytes stimulated by various capacitively coupled electric field amplitudes, all for 30 minutes duration. This example shows that the differences between the field amplitude specificity of aggrecan mRNA (FIG. 3) and the amplitude specificity of Type II collagen mRNA allow for selectivity of signals.

FIG. 7 is a graphic representation of Type II collagen mRNA production in articular chondrocytes amplitudes, all for 30 minutes duration. As illustrated, 20, 40, and 2 mV/cm all showed significant increases in Type II collagen mRNA. It is also noteworthy that the differences between the field amplitude specificity of aggrecan mRNA (FIG. 3) and the amplitude specificity of Type II collagen mRNA allow for selectivity of signals. For example, one could selectively choose a 10 mV/cm signal to stimulate aggrecan mRNA if one did not want to stimulate Type II collagen mRNA, or a 2 mV/cm or a 40 mV/cm signal to stimulate Type II collagen mRNA if one did not want to stimulate aggrecan mRNA This data shows that the specificity of the applied signals allows one to obtain a specific gene expression.

With reference to Examples 1 and 2, it is demonstrated that each of those genes encoding aggrecan or Type II collagen can be regulated by an identical 20 mV/cm, 60 kHz capacitively coupled signal. Those skilled in the art will appreciate that each of these gene transcripts regulates cartilage matrix formation and are functionally complementary. Accordingly, the findings of examples 1 and 2 are believed to support electrical therapy through gene regulation in accordance with the techniques described herein.

Example 3

MMP-1 mRNA Production In IL-$\beta_1$ Treated Articular Chondrocytes

Articular chondrocytes were exposed to a capacitively coupled electric signal of 20 mV/cm at 60 kHz. The results are illustrated in FIG. 8.

Figure 8:
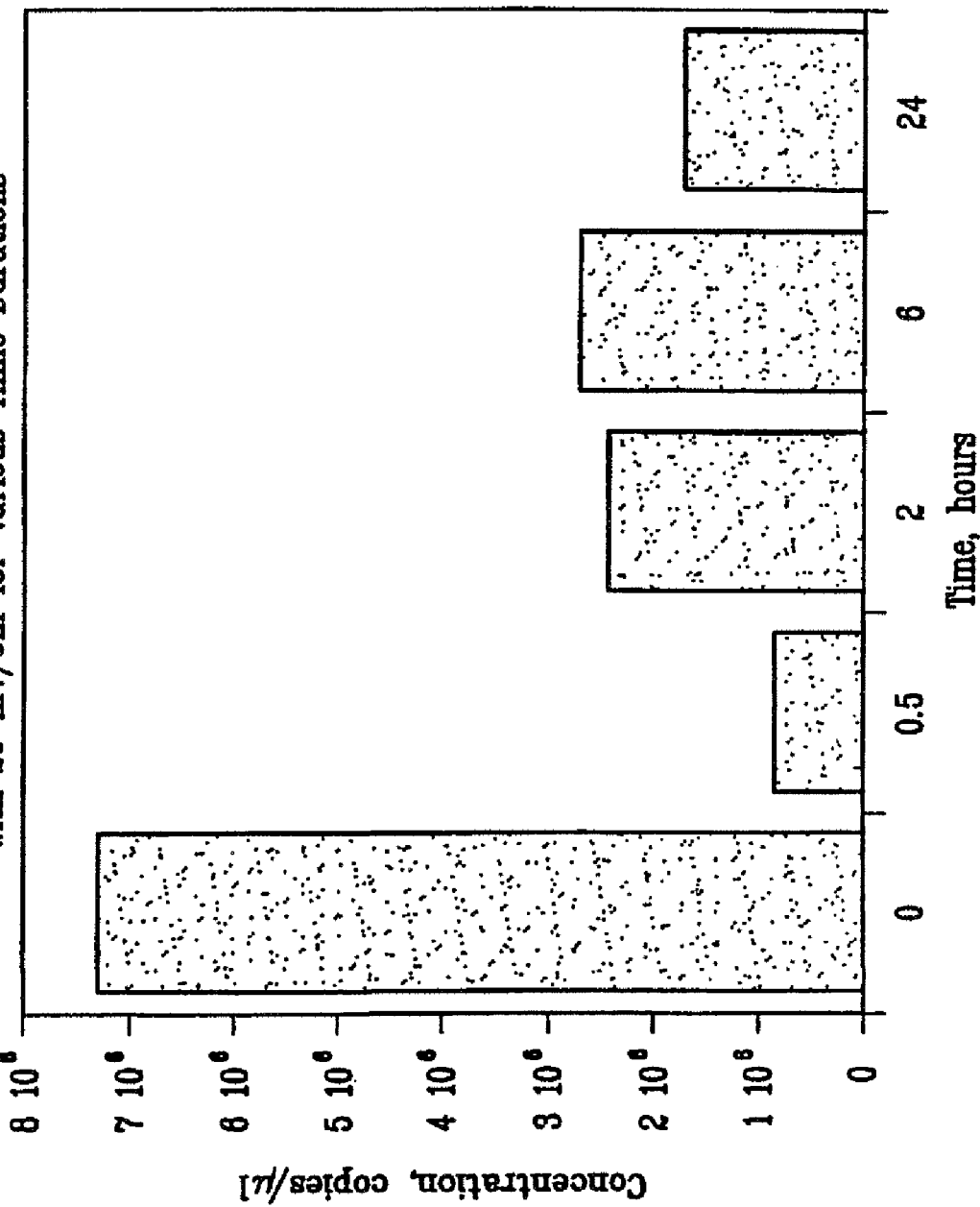
FIG. 8 is a graphic representation of the down-regulation of MMP-1 mRNA production by articular cartilage chondrocytes treated with IL-$\beta_1$ and stimulated with a 20 mV/cm capacitively coupled field for various time durations. This example shows the selectivity and specificity of these electric fields whereby a specific signal must be used for a selected gene response.

FIG. 8 is a graphic representation of MMP-1 mRNA production by articular cartilage chondrocytes treated with IL-$\beta_1$ and stimulated with a 20 mV/cm (60 kHz) capacitively coupled field for time durations of 0 (control), 0.5, 2, 6, and 24 hours. As illustrated, MMP-1 mRNA is dramatically down-regulated in all time durations of stimulation, but especially so at 30 minutes. This is significant when contrasted with the dramatic up-regulation of aggrecan mRNA (FIGS. 1-4) and Type II collagen mRNA (FIGS. 5-7) in the same 20 mV/cm field. This shows the selectivity and specificity of these electric fields whereby a specific signal must be used for a selected gene response.

Example 4

MMP-3 mRNA Production In IL-$\beta_1$ Treated Articular Chondrocytes

Articular chondrocytes were exposed to a capacitively coupled electric signal of 20 mV/cm at 60 kHz. The results are illustrated in FIG. 9.

Figure 9:
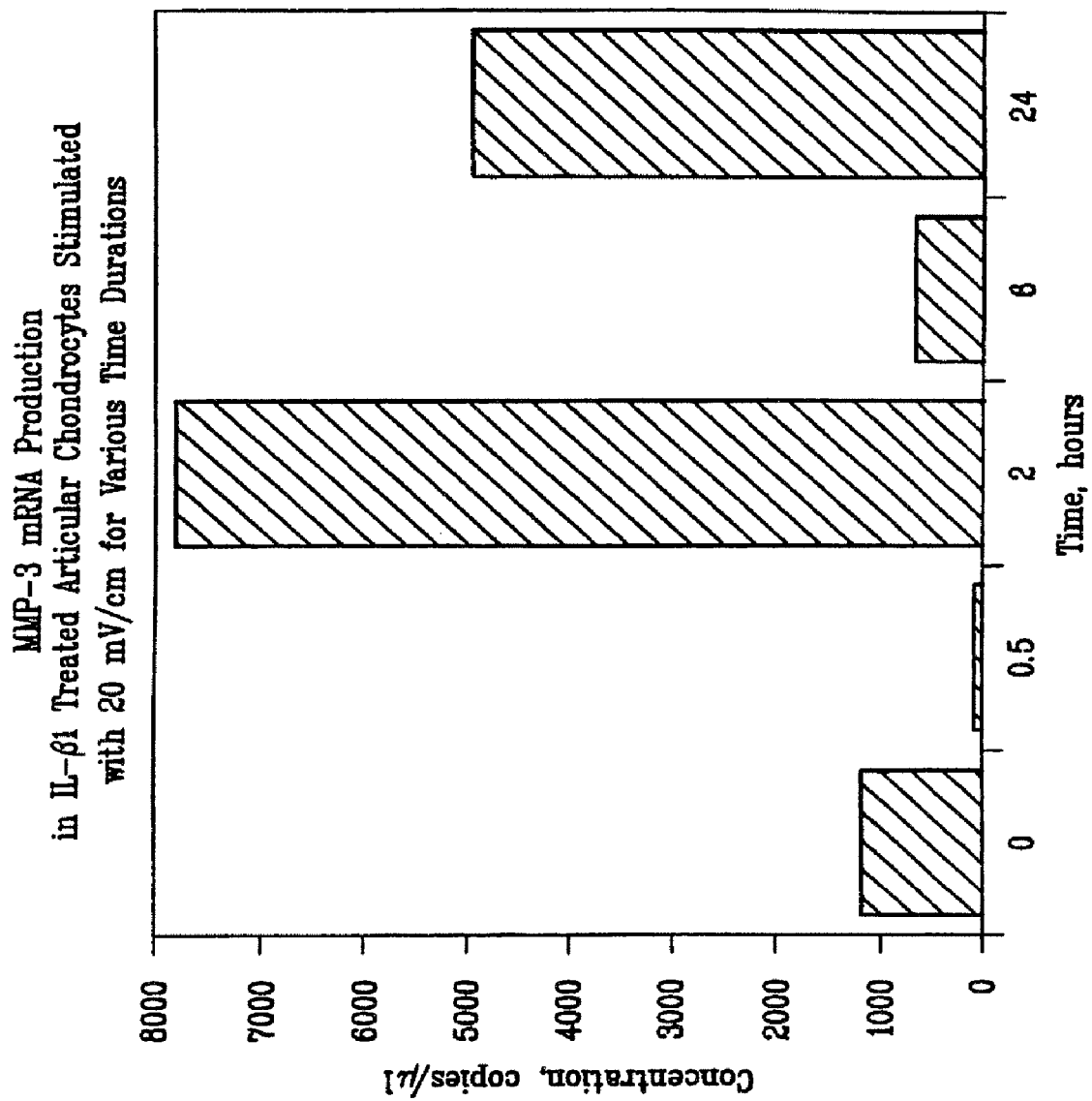
FIG. 9 is a graphic representation of MMP-3 mRNA production by articular cartilage chondrocytes stimulated with a 20 mV/cm capacitively coupled electric field for various time durations. This example illustrates the significance of time specificity in the application of these signals.

FIG. 9 is a graphic representation of MMP-3 mRNA production by articular cartilage chondrocytes stimulated with a 20 mV/cm (60 kHz) capacitively coupled electric field for time durations of 0 (control), 0.5, 2,6, and 24 hours. As illustrated, there is significant down-regulation of MMP-3 mRNA with 30 minutes of stimulation and a dramatic up-regulation with 2 hours of stimulation. This points out the significance of time specificity in the application of these signals.

Example 5

TGF-$\beta_1$ Production By Bone Cells

As noted above, it has been reported that a 60 kHz capacitively coupled electric field of 20 mV/cm produces a significant increase in TGF-$\beta_1$ in similar bone cells. Brighton et al., *Biochem. Biophys. Res. Commun.* 237: 225-229 (1997). It was found that there was significant production of TGF-$\beta_1$ mRNA, but only after 6 hours of stimulation (in contrast to 0.5 hours for aggrecan mRNA and Type II collagen mRNA). The experiment was repeated to determine if the exposure of MC3T3-E1 bone cells to the 20 mV/cm, 60 kHz capacitively coupled electric signal had an effect on the production of PDGF-A mRNA. No effect was found.

Thus, a 20 mV/cm, 60 kHz capacitively coupled signal regulates bone cell genes encoding TGF-$\beta_1$ but fails to regulate genes encoding PDGF-A. It is presently believed that the expression of each of these genes participates in the regulation of different phases and physiologic processes of bone healing and are thus are not functionally complementary.

Example 6

Treatment Of Osteoarthritis

With reference to FIG. 10, a device 10 in accordance with preferred embodiments of the present invention is used to treat a patient with osteoarthritis of the knee. As illustrated, two circular, soft conductive, self-adherent electrodes 12 are placed on the skin on either side of the knee at the level of the joint line. The electrodes 12 are attached to a power unit 14 which has a Velcro patch 16 on the reverse side such that the power unit 14 can be attached to a Velcro strap (not shown) fitted around the calf, thigh or waist. The electrodes 12 may be placed on the skin before the patient goes to bed each evening or any other convenient time.

The power unit is preferably small (e.g., 6-8 ounces) and powered by a standard 9-volt battery to emit a 5 volt peak-to-peak, 6-10 mump, 20 mV/cm, 60 kHz sine wave signal to the electrodes 12 placed on the skin. As illustrated in the above examples, this signal provided 30 minutes per day with the proper time duration, field amplitude, and duty cycle should significantly up-regulate genes encoding aggrecan and Type II collagen. This treatment should prevent or minimize further articular cartilage deterioration as well as heal articular cartilage that already is damaged or degenerated.

The power unit 14 also may be reconfigured to provide signals specific and selective for other genes. For example, as illustrated in the above examples, the power unit 14 may be reconfigured to provide signals for down-regulating the gene expression of metalloproteinase (MMP) as well as signals for up-regulating genes expressing tissue inhibitors of metalloproteinase ("TIMP") genes. The power unit 14 may be reconfigured to provide such signals in sequence with the aggrecan/Type II collagen signal. Accordingly, the patient may be treated through the up-regulation of genes that repair cartilage (e.g., aggrecan and Type II collagen genes), down-regulation of genes that destroy cartilage (e.g., metalloproteinase gene) and the up-regulation of genes that inhibit the metalloproteinases that destroy articular cartilage (e.g., tissue inhibitors of metalloproteinase).

Example 7

Treatment Of Bone Defects Or Osteoporosis

With reference to FIG. 11, a patient with a fracture, delayed union, nonunion or other bone defect may be treated with two circular, soft conductive electrodes 12 placed on the skin on opposite sides of the extremity at the level of the defect. The electrodes 12 are placed on the skin so as to span the bone defect. The electrodes 12 are attached to a power unit 14' which has a Velcro patch 16 on the reverse side such that the power unit 14' can be attached to a Velcro strap (not shown) fitted around the calf, thigh or waist. In accordance with preferred embodiments of the invention, a nonunion of the femur may be stabilized by an intramedullary rod 18 locked by two transcortical screws 20, as shown in FIG. 11.

The power unit 14' provides a 20 mV/cm, 60 kHz sine wave signal to the electrodes 12 placed on the skin. The signal is provided for 6 hours per day as in example 5. The power unit 14' is differentiated from power unit 14 in the previous example since the same electrical signal as defined by time duration, field amplitude, and duty cycle is not necessarily applied. This technique should aid in the repair process by up-regulating TGF-$\beta_1$, a gene important in the cartilage phase of bone repair.

Those skilled in the art will appreciate that the power unit 14' may be reconfigured to provide other signals specific for certain genes. For example, the power unit 14 may be reconfigured to provide signals for the up-regulation of PDGF-A, basic FGF and BMP-2 genes. The power unit 14 also may be reconfigured to provide in sequence those signals specific and selective for TGF-$\beta_1$, PDGF-A, basic FGF, and BMP-2 genes. Therefore, the power unit 14 may be reconfigured to provide specific and selective signals that up-regulate genes necessary to heal bone defects.

Example 8

Treatment Of Tumors

With reference to FIG. 12, a patient with malignant melanoma may be treated with methods and devices according to preferred embodiments of the present invention. FIG. 12 shows a patient with malignant melanoma that has not yet broken out of the skin into the underlying tissue. As discussed above, in a patient with a primary (or even metastatic) cancer, spread of the cancer takes place by metalloproteinases, which are produced by cancer cells. Metalloproteinases enzymatically break down the fibrous wall or membrane that adjacent cells establish in an attempt to contain the cancer. As discussed above, tissue inhibitors of metalloproteinase may inhibit the production of such metalloproteinases.

The device 10" of the invention provides specific capacitively coupled electric fields via electrodes 12 for selectively down-regulating the gene encoding for metalloproteinase as discussed in the above examples and/or selectively up-regulating the gene encoding for tissue inhibitors of metalloproteinase ("TIMP"). The device 10" can provide the electric field generated by power unit 14" so as to selectively down-regulate and up-regulate the genes sequentially for specific periods of time per day. The melanoma can be safely excised once the melanoma has been sufficiently encapsulated by the body's own defensive mechanism.

Those skilled in the art will also appreciate that numerous other modifications to the invention are possible within the scope of the invention. For example, genes encoding for tissue inhibitors of metalloproteinase ("TIMP") and other genes may have improved specific dose responses at selective frequencies other than 60 kHz so as to provide specific and selective responses for applied signals at different frequencies with different time durations, field amplitudes, and duty cycles. Also, as noted above, inductively coupled signals, direct coupled signals, and pulsed electromagnetic fields may also be applied in lieu of capacitively coupled signals as described in the examples above. Accordingly, the scope of the invention is not intended to be limited to the preferred embodiment described above, but only by the appended claims.

What is claimed:

1. A device for the treatment of injured or diseased tissue comprising a signal source that generates a signal for application to a field generating device connected to the signal source so as to receive said signal and that is operatively disposed with respect to the injured or diseased tissue, said field generating device upon receipt of said signal causing the generation of an electric field having an amplitude of about 2-40 mV/cm in the injured or diseased tissue that is specific and selective for gene expression of at least one gene of the injured or diseased tissue, said signal source controlling and varying duration of time of application of said signal per 24 hour period and controlling and varying the duty cycle of said signal applied to said field generating device so as to optimize the selective regulation of the gene expression of said at least one gene in the injured or diseased tissue as a result of application of the specific and selective electric field.

2. The device of claim 1 further comprising a portable power unit that drives said signal source.

3. The device of claim 1 further comprising means for attaching the field generating device to a body of a patient in the vicinity of the injured or diseased tissue.

4. The device of claim 1 wherein the signal is an electrical or electromagnetic signal.

5. The device of claim 1 wherein the specific and selective electric field is applied to said injured or diseased tissue as a direct current, as a combined field, via capacitive coupling, or inductive coupling.

6. The device of claim 1 wherein the specific and selective electric field has an amplitude of about 20 mV/cm at 60 kHz in the injured or diseased tissue.

7. A device as in claim 1, wherein the signal is selected to regulate the gene expression of at least one of aggrecan, tissue inhibitors of metalloproteinase, metalloproteinase, type II collagen mRNA, TGF-β mRNA, PDGF-A, basic FGF, and BMP-2.

8. A device as in claim 1, wherein said field generating device comprises at least one electrode or at least one coil.

* * * * *